United States Patent
Eliav et al.

(10) Patent No.: US 7,386,905 B2
(45) Date of Patent: *Jun. 17, 2008

(54) POWERED TOOTHBRUSH

(75) Inventors: Eyal Eliav, New York, NY (US); John J. Gatzemeyer, Hillsborough, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/733,155

(22) Filed: Apr. 9, 2007

(65) Prior Publication Data

US 2007/0174978 A1    Aug. 2, 2007

Related U.S. Application Data

(60) Division of application No. 11/218,679, filed on Sep. 2, 2005, now Pat. No. 7,210,184, which is a continuation of application No. 10/963,716, filed on Oct. 14, 2004, now Pat. No. 6,938,293, which is a division of application No. 10/128,617, filed on Apr. 23, 2002, now abandoned.

(51) Int. Cl.
*A61C 17/22*    (2006.01)

(52) U.S. Cl. ............................... 15/22.1; 15/28

(58) Field of Classification Search ............. 15/22.1, 15/22.2, 22.4, 28, 29; 601/142; D4/101
See application file for complete search history.

(56) References Cited

U.S. PATENT DOCUMENTS

| | | |
|---|---|---|
| 1,191,556 A | 7/1916 | Blake |
| 1,720,017 A | 7/1929 | Touchstone |
| 1,918,521 A | 7/1933 | Chott |
| 2,059,914 A | 11/1936 | Rosenberg |
| 2,088,839 A | 8/1937 | Coney et al. |
| 2,117,174 A | 5/1938 | Jones |
| 2,129,082 A | 9/1938 | Byrer |
| 2,140,307 A | 12/1938 | Belaschk et al. |
| 3,195,537 A | 7/1965 | Blasi |
| 3,242,516 A | 3/1966 | Cantor |
| 3,619,845 A | 11/1971 | Partridge et al. |
| 4,277,862 A | 7/1981 | Weideman |
| 4,827,550 A | 5/1989 | Graham et al. |
| 4,845,795 A | 7/1989 | Crawford et al. |
| 4,989,287 A | 2/1991 | Scherer |
| D321,285 S | 11/1991 | Hirabayashi |
| 5,070,567 A | 12/1991 | Holland |
| 5,088,145 A | 2/1992 | Whitefield |
| 5,099,536 A | 3/1992 | Hirabayashi |
| 5,170,525 A | 12/1992 | Cafaro |

(Continued)

FOREIGN PATENT DOCUMENTS

EP    1053721    * 11/2000

(Continued)

*Primary Examiner*—Mark Spisich
(74) *Attorney, Agent, or Firm*—Michael J. Wallace, Jr.

(57) ABSTRACT

A powered toothbrush include a head containing a rotating or oscillating first bristle carrier and also containing a second bristle carrier movably connected to the head, which second bristle carrier may include elastomeric walls for enhanced cleaning and may include a weakened section to permit it to at least partially collapse during a brushing motion.

17 Claims, 14 Drawing Sheets

U.S. PATENT DOCUMENTS

| | | |
|---|---|---|
| 5,226,206 A | 7/1993 | Davidovitz et al. |
| 5,276,932 A | 1/1994 | Byrd |
| 5,353,460 A | 10/1994 | Bauman |
| 5,416,942 A | 5/1995 | Baldacci et al. |
| 5,504,959 A | 4/1996 | Yukawa et al. |
| 5,524,312 A | 6/1996 | Tan et al. |
| 5,535,474 A | 7/1996 | Salazar |
| 5,604,951 A | 2/1997 | Shipp |
| 5,617,603 A | 4/1997 | Mei |
| 5,727,273 A | 3/1998 | Pai |
| 5,732,433 A | 3/1998 | Gocking et al. |
| 5,778,474 A | 7/1998 | Shek |
| 5,799,354 A | 9/1998 | Amir |
| 5,842,244 A | 12/1998 | Hilfinger et al. |
| 5,842,245 A | 12/1998 | Pai |
| 5,850,655 A | 12/1998 | Gocking et al. |
| 6,032,313 A | 3/2000 | Tsang |
| 6,041,467 A | 3/2000 | Roberts et al. |
| 6,105,191 A | 8/2000 | Chen et al. |
| 6,138,310 A | 10/2000 | Porper et al. |
| 6,148,462 A | 11/2000 | Zseng |
| 6,209,164 B1 | 4/2001 | Sato |
| 6,311,358 B1 | 11/2001 | Soetewey et al. |
| 6,334,232 B1 | 1/2002 | Sato |
| 6,343,396 B1 | 2/2002 | Simovitz et al. |
| 6,349,442 B1 | 2/2002 | Cohen et al. |
| D456,139 S | 4/2002 | Hohlbein |
| 6,381,794 B1 | 5/2002 | Porper et al. |
| 6,401,288 B1 | 6/2002 | Porper et al. |
| 6,421,867 B1 | 7/2002 | Weihrauch |
| 6,434,773 B1 | 8/2002 | Kuo |
| 6,446,295 B1 | 9/2002 | Calabrese |
| 6,453,499 B1 | 9/2002 | Leuermann |
| 6,463,615 B1 | 10/2002 | Gruber et al. |
| 6,463,618 B1 | 10/2002 | Zimmer |
| 6,463,619 B2 | 10/2002 | Gavney, Jr. |
| 6,510,575 B2 | 1/2003 | Calabrese |
| 6,513,182 B1 | 2/2003 | Calabrese et al. |
| 6,564,940 B2 | 5/2003 | Blaustein et al. |
| D476,157 S | 6/2003 | Gatzemeyer et al. |
| 6,571,417 B1 | 6/2003 | Gavney, Jr. et al. |
| 6,574,820 B1 | 6/2003 | DePuydt et al. |
| D477,715 S | 7/2003 | Gatzemeyer et al. |
| 6,599,048 B2 | 7/2003 | Kuo |
| D478,214 S | 8/2003 | Winkler et al. |
| D479,402 S | 9/2003 | Gatzemeyer et al. |
| 6,654,979 B2 | 12/2003 | Calabrese |
| 2001/0020314 A1 | 9/2001 | Calabrese |
| 2002/0059685 A1 | 5/2002 | Paffrath |
| 2002/0124337 A1 | 9/2002 | Calabrese et al. |
| 2002/0138928 A1 | 10/2002 | Calabrese |
| 2002/0152563 A1 | 10/2002 | Sato |
| 2002/0152564 A1 | 10/2002 | Blaustein et al. |
| 2002/0157198 A1 | 10/2002 | Biro et al. |
| 2003/0033680 A1 | 2/2003 | Davies et al. |
| 2003/0033682 A1 | 2/2003 | Davies et al. |
| 2003/0074751 A1 | 4/2003 | Wu |
| 2003/0077107 A1 | 4/2003 | Kuo |
| 2003/0084524 A1 | 5/2003 | Blaustein et al. |
| 2003/0084525 A1 | 5/2003 | Blaustein et al. |
| 2003/0084526 A1 | 5/2003 | Brown et al. |
| 2003/0084527 A1 | 5/2003 | Brown et al. |
| 2003/0084528 A1 | 5/2003 | Chan et al. |
| 2003/0126699 A1 | 7/2003 | Blaustein et al. |
| 2003/0126700 A1 | 7/2003 | Jeng et al. |
| 2003/0140435 A1 | 7/2003 | Eliav et al. |
| 2003/0140436 A1 | 7/2003 | Gatzemeyer et al. |
| 2003/0140437 A1 | 7/2003 | Eliav et al. |
| 2003/0140440 A1 | 7/2003 | Gavney, Jr. |
| 2003/0154568 A1 | 8/2003 | Boland et al. |
| 2003/0159224 A1 | 8/2003 | Fischer et al. |
| 2003/0163881 A1 | 9/2003 | Driesen et al. |
| 2003/0163882 A1 | 9/2003 | Blaustein et al. |
| 2003/0182743 A1 | 10/2003 | Gatzemeyer et al. |
| 2003/0182744 A1 | 10/2003 | Fattori et al. |
| 2003/0182746 A1 | 10/2003 | Fattori et al. |
| 2003/0182747 A1 | 10/2003 | DePuydt |
| 2003/0192139 A1 | 10/2003 | Fattori et al. |
| 2003/0208865 A1 | 11/2003 | Davies |
| 2003/0221270 A1 | 12/2003 | Kuo |
| 2003/0226223 A1 | 12/2003 | Chan |
| 2003/0229959 A1 | 12/2003 | Gavney, Jr. et al. |
| 2004/0010869 A1 | 1/2004 | Fattori et al. |

FOREIGN PATENT DOCUMENTS

| | | | |
|---|---|---|---|
| GB | 2319170 | * | 5/1998 |

* cited by examiner

POWERED TOOTHBRUSH

CROSS REFERENCE TO RELATED APPLICATIONS

This application is a divisional application of U.S. patent application Ser. No. 11/218,679 filed Sep. 2, 2005, now U.S. Pat. No. 7,210,184 which is a continuation of the U.S. patent application Ser. No. 10/963,716, filed Oct. 14, 2004, now U.S. Pat. No. 6,938,293, which is a divisional application of U.S. patent application Ser. No. 10/128,617 filed Apr. 23, 2002 now abandoned, the contents of said application is hereby incorporated by reference.

BACKGROUND OF THE INVENTION

1. Field of the Invention

The present invention relates to powered toothbrushes, and more particularly, to a toothbrush having a head with two distinct sections that each provides cleaning and/or massaging oral health benefits to the soft and hard tissues of the mouth.

2. Discussion of Related Art

Toothbrushes provide many oral hygiene benefits, including for example, toothbrushes remove plaque and food debris to help avoid tooth decay and disease. They remove stained pellicle from the surface of each tooth to help whiten the teeth. Also, the bristles combined with the brushing motion massage the gingival tissue for stimulation and increased health of the tissue.

Powered toothbrushes have been available for some time. Powered toothbrushes have advantages over manual (non-powered) toothbrushes in that they impart movement to the bristles at much higher speeds than possible manually. They also may impart different types and directions of motion. These motions, in combination with manual movement of the toothbrush by the user, generally provides superior cleaning than manual toothbrushes. Typically, powered toothbrushes are powered by disposable or rechargeable batteries that power an electric motor that in turn drives the toothbrush head.

Known powered toothbrushes include a brush head with a bristle carrier portion that rotates, oscillates or vibrates in some manner so as to clean the teeth. The bristles, which typically comprise bristle tufts, are generally uniform with one end fixed into the bristle carrier portion and the other end free to contact the surface of the teeth while brushing. The free ends of the various tufts present a surface envelope that is capable of some deformation when the bristles bend. When in contact with the surface to be brushed, the bristles may deform so that the surface envelope tends to conform to the complex surface of the teeth. Human teeth generally lie in a "C" shaped curve within the upper and lower jaw, and each row of teeth consequently has a convex outer curve and a concave inner curve. Individual teeth often have extremely complex surfaces, with areas that may be flat concave, or convex. The more precise conformation between the bristles and the tooth surface, the more effective the toothbrush may be in cleaning, whitening and/or stimulating.

Known powered toothbrushes typically arrange the bristles in a compact conical or cylindrical pattern on a generally circular, disk-shaped bristle carrier. The powered toothbrush heads are traditionally compact, generally circular face from which a flat trimmed bristle pattern extends. Alternatively, other head shapes and bristle patterns are available.

One example of a powered toothbrush is depicted in U.S. Pat. No. 5,625,916 to McDougall, which is hereby incorporated by reference in its entirety. The toothbrush shown in McDougall has a disc-shaped bristle carrier. The bristle carrier, and thus the bristles, are driven in a vibrating or oscillating manner. This type of toothbrush is described herein with reference to FIGS. 1A-1C. A toothbrush 5 includes a handle portion 10 at a proximal of the toothbrush 5 and a head 11 at a distal end of the toothbrush 5. The handle portion 10 has compartments for containing a powered motor 14 and batteries 15 and 16. The head 11 includes a generally circular bristle holder (carrier) 13. A rotatable shaft 12 extends from the motor 14 to the head 11. A shaft coupling 17 may be located along the shaft 12 and configured to provide for the shaft 12 to be separated at a point between the motor 14 and the head 11. This permits the head 11 to be removed from the toothbrush 5, e.g., for cleaning, servicing, or replacement.

The head 11 includes a post 18 that provides a rotational pivot axis for the bristle holder 13 containing bristle tufts 19. The distal end of the shaft 12 has a journal or offset 20 that is radially displaced from the longitudinal axis of the shaft 12, which may be integrally formed therewith. The bristle holder 13 has a slot 22 that receives the offset 20. The offset 20 and slot 22 are configured so as to be oriented toward the intersection of the shaft 12 axis and the longitudinal axis of the post 18. When the motor 14 rotates the shaft 12, the motion of the offset 20 defines a circle about the shaft 12 axis and drivingly engages the slot 22 such that the bristle holder 13 vibrates or oscillates about the post 18 axis through a rotational angle A. The rotational angle A is defined by the displacement of the offset 20 from the shaft 12 axis relative to the diameter of the bristle holder 13.

Although powered toothbrushes such as those described immediately above provide advantages over manual toothbrushes, they are subject to various limitations. Providing a rotating or oscillating bristle holder (crier) with a typical circular, oblong or oval toothbrush head constrains the size of the moving bristle holder, and consequently the area of bristles available for teeth cleaning. Also, when the bristles are placed in contact with the teeth during brushing, there is less bristle contact with adjacent areas, such as the gums. Thus, while these compact bristle patterns provide for cleaning, there is minimal whitening and stimulation.

One attempt to overcome the limitations associated with a small powered bristle area is shown in U.S. Pat. No. 6,000,083 to Blaustein et al. The toothbrush in Blaustein et al. has a bristle area and pattern similar to a manual toothbrush, but an area of the bristles has simply been replaced by a powered bristle section. The result is that the head has a powered or moving bristle section and static bristle section. The limitation of Blausetein et al. is that the static bristle section provides no better cleaning, whitening or stimulation than a manual toothbrush.

International Application No. PCT/EP01/07615 of Braun GmbH discloses a powered toothbrush with two separate bristle parts that can move. Each bristle part cam have a different range and/or type of motion However, only one bristle part is powered. The other unpowered bristle part moves due to a resonance effect imparted by the frequency of the movement of the first bristle part. This free resonance causes a number of difficulties. First, because any contact between the bristle parts will dampen or cancel any resonance of the unpowered bristle part, the unpowered bristle part "floats" separately from the powered bristle part. This necessitates separation or gaps between then. These gaps expose the internal wok of the head to foreign matter such as water, saliva, toothpaste, and food particles. This foreign matter may interfere with the workings of the unpowered bristle head. For example, the unpowered bristle part is spring-loaded to assist its resonance. Foreign matter may accumulate on or around the spring, interfering with its function. In addition, food particles may remain in the head and may fester and host microorganisms, which are undesirable if not potentially harmful when introduced directly into the mouth. Another limitation of such a design is that movement of the unpowered bristle part may be damped by contact with the teeth, or lessened when the frequency of the powered part shifts from the resonance frequency. This can occur due to pressure imparted against the powered bristle part by the teeth or gums during brushing. Finally, the energy imparted to the unpowered bristle part is only a portion of the energy input into the powered part. Therefore, the unpowered bristle part is less effective in cleaning than the powered part, limiting the overall effectiveness of the toothbrush.

Thus, there is a need in the art for a powered toothbrush with increased effectiveness through a larger area of powered or driven bristles or bristles that are otherwise movable. There is also a need for a toothbrush having increased whitening and/or stimulation than own toothbrushes. There is further a need for such improved toothbrushes to be comparable in manufacturing and purchasing costs as known powered toothbrushes.

SUMMARY OF THE INVENTION

A powered toothbrush is provided and includes a handle portion at a proximal end and a head at a distal end with a neck being formed between the handle portion and the head. According to one embodiment, the head has two distinct movable parts that provide cleaning and/or massaging oral health benefits since each is adapted to have a number of bristles or elastomeric cleaning members extending therefrom to contact surfaces of the teeth and surrounding areas. The toothbrush has a drive mechanism that imparts movement to the first movable part to deliver a cleaning, polishing, whitening action that supplements the cleaning efficiency of a typical powered toothbrush.

In one embodiment, the first movable head part is a first bristle carrier that supports at least one set of bristle tufts. The first bristle carrier is operatively mounted to the head and is coupled to the drive mechanism such that the first bristle carrier rotates and/or oscillates back and forth in a direction parallel to the toothbrush head. Preferably, the first bristle carrier oscillates back and forth in a rotational direction. The second movable part is in the form of a second bristle carrier that includes a platform (formed of a rigid and/or elastomeric material) that is operatively mounted to the head and includes upstanding elastomeric walls formed at first and second sides of the platform. The second bristle carrier also preferably includes at least one set of bristles disposed between the upstanding elastomeric walls. During a brushing motion, the bristles and elastomeric walls flex as they encounter the teeth and gingival tissue to provide the oral care benefits that are disclosed herein.

In another exemplary embodiment, the platform has a weakened section formed therein in a direction that is parallel to a longitudinal axis of the head such that upon application of a force to the second bristle carrier, the platform at least partially collapses along the weakened section. This results in movement (e.g., inward flexing) of the elastomeric walls and the at least one set of bristles to provide oral care benefits.

In yet another embodiment, the second bristle carrier has an "I-beam" construction in that it includes a platform extending across the head and a web that connects the platform to the head. The platform includes at least one set of bristles extending upwardly therefrom. According to one configuration, at least the web is formed of an elastomeric material to permit the platform and at least one set of bristles formed as a part thereof to flex and move during a brushing motion. It will also be appreciated that the platform can also be formed of an elastomeric material and/or a rigid material used in combination with a web that is formed of a rigid material and/or an elastomeric material. The platform can also include elastomeric side walls that flex during the brushing motion.

Other features and advantages of the present invention will be apparent from the foregoing detailed description when read in conjunction with the accompanying drawings.

BRIEF DESCRIPTION OF THE DRAWING FIGURES

The foregoing and other features of the present invention will be more readily apparent from the following detailed description and drawings of illustrative embodiments of the invention in which:

FIGS. 4A-4C are a top plan view and elevated cross-section views of an alternate embodiment of the powered toothbrush head of the powered toothbrush embodiment of FIG. 3, in motion;

FIG. 19B is a perspective view of an elastomeric tooth care element having a fifth configuration and adapted for use in the toothbrush head.

DETAILED DESCRIPTION OF THE EMBODIMENT

Figure 1A:
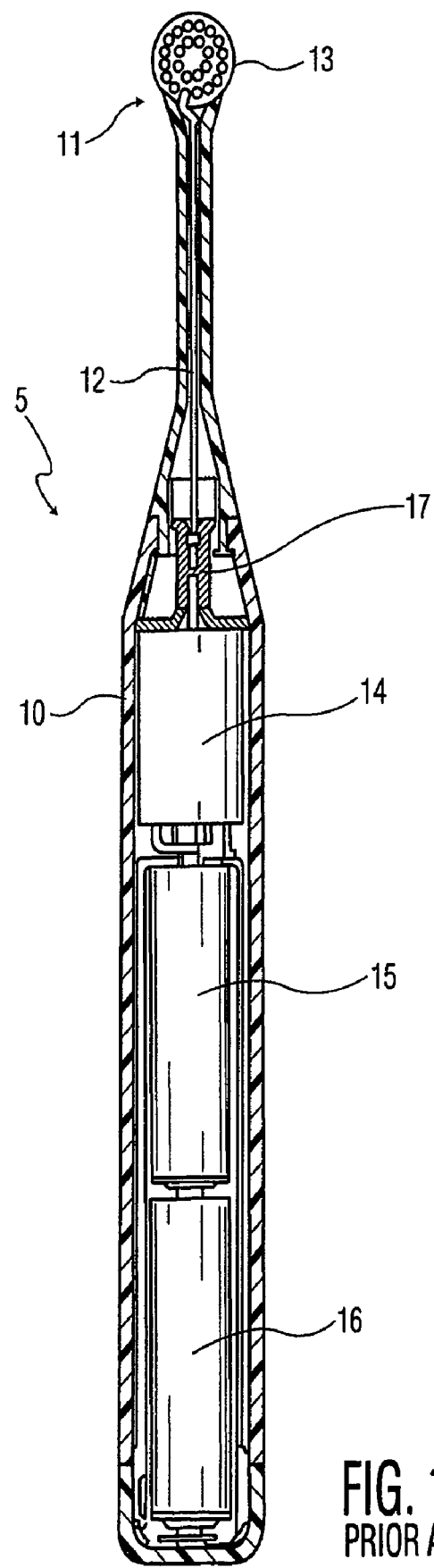
FIG. 1A is a front cross-sectional view of a conventional powdered toothbrush including a head.

Referring first to FIGS. 2 through 11 in which an exemplary powered toothbrush according to a first embodiment is illustrated and generally indicated at 100. The toothbrush 100 includes a handle 102 at a proximal end that defines an interior compartment (not illustrated) for housing various toothbrush components and a brush section 104 that is defined by a neck 110 that terminates in a head 120 at a distal end of the toothbrush 100. The handle 102 has a free proximal end 108 and an opposite neck end 106. The neck 110 generally extends from a first end 114 to a second end 116 with the first end 114 being located at the neck end 106 of the handle 102 and the second end 116 being located at the head 120. In other words, the neck 110 is the portion of the toothbrush 100 that extends between the handle 102 and the head 120. The neck 110 also defines an interior compartment (not illustrated) for housing various working components of the toothbrush 100. The head 120 is may be generally aligned with the longitudinal axis of the toothbrush 100 or may be mounted on a neck 110 with is angled with respect to said handle 102.

According to one embodiment, the neck 110 and the handle 102 are constructed as a unitary member by forming the neck 110 integral to the handle 102 at the neck end 106 of the handle 102. In another embodiment, the neck 110 is detachable from the handle 102 at the neck end 106 of the neck 110. In this embodiment, the combined neck 110 and head 120 can be removed from the handle 102 to permit cleaning, servicing and/or interchanging of either the handle 102 or the combined neck 110 and head 120. When the neck 110 is detachable from the handle 102, i.e. a replaceable head 120/neck 110 assembly, the first neck end 114 can include a connector (not illustrated) that is adapted to be detachably joined to the handle 102 using traditional techniques.

It will further be appreciated that the illustrated shapes of the handle 102 and neck 110 are merely exemplary in nature and the handle 102 and/or neck 110 can be formed to have any number of shapes. Preferably, the shapes of the handle 102 and the neck 110 are ergonomically efficient and pleasing to a user of the toothbrush 100 and provide a toothbrush that is easily gripped, held and manipulated by the use. For example, the handle 102 can include slightly recessed finger sections 118 which are formed on opposite sides of the handle 102. One recessed finger section 118 is designed to receive the thumb of one hand and the other recessed finger section 118 is designed to receive one or more other fingers of the same hand to thereby assist the user in proper placement of the toothbrush 100 in the user's hand. One or more of the recessed finger sections 118 can include ribs or another type of roughened surface to assist the user in gripping the toothbrush in the recessed finger sections 118.

As illustrated in FIGS. 3, 9, 10, 11, et seq., the head 120 of the toothbrush 100 includes a head base 160 that partially defines an inner compartment of the head 120. The head base 160 can be constructed so that it terminates in a rounded distal end 162, which actually defines the distal end of the toothbrush 100. Preferably, the head base 160 is integrally attached to the second end 116 of the neck 110.

Figure 1B:
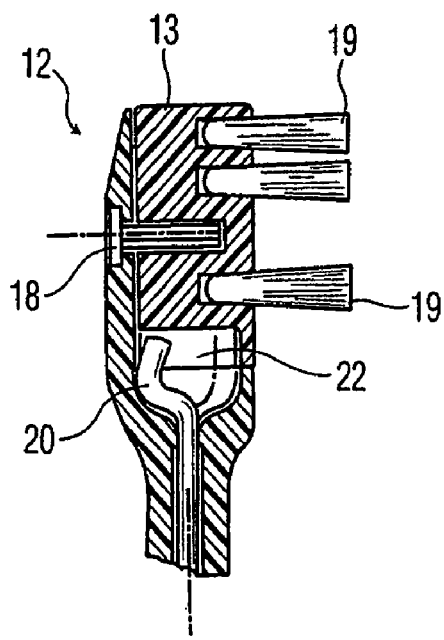
FIG. 1B is a partial cross-sectional side view of the toothbrush head of FIG. 1A.
Figure 1C:
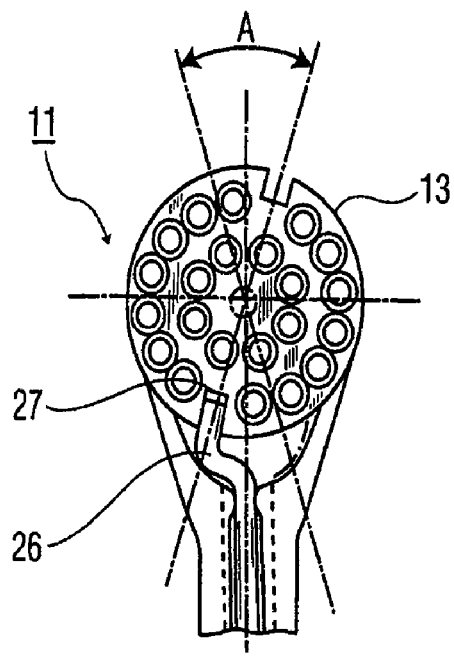
FIG. 1C is a partial cross-sectional front view of the toothbrush head of FIG. 1A.
Figure 2:
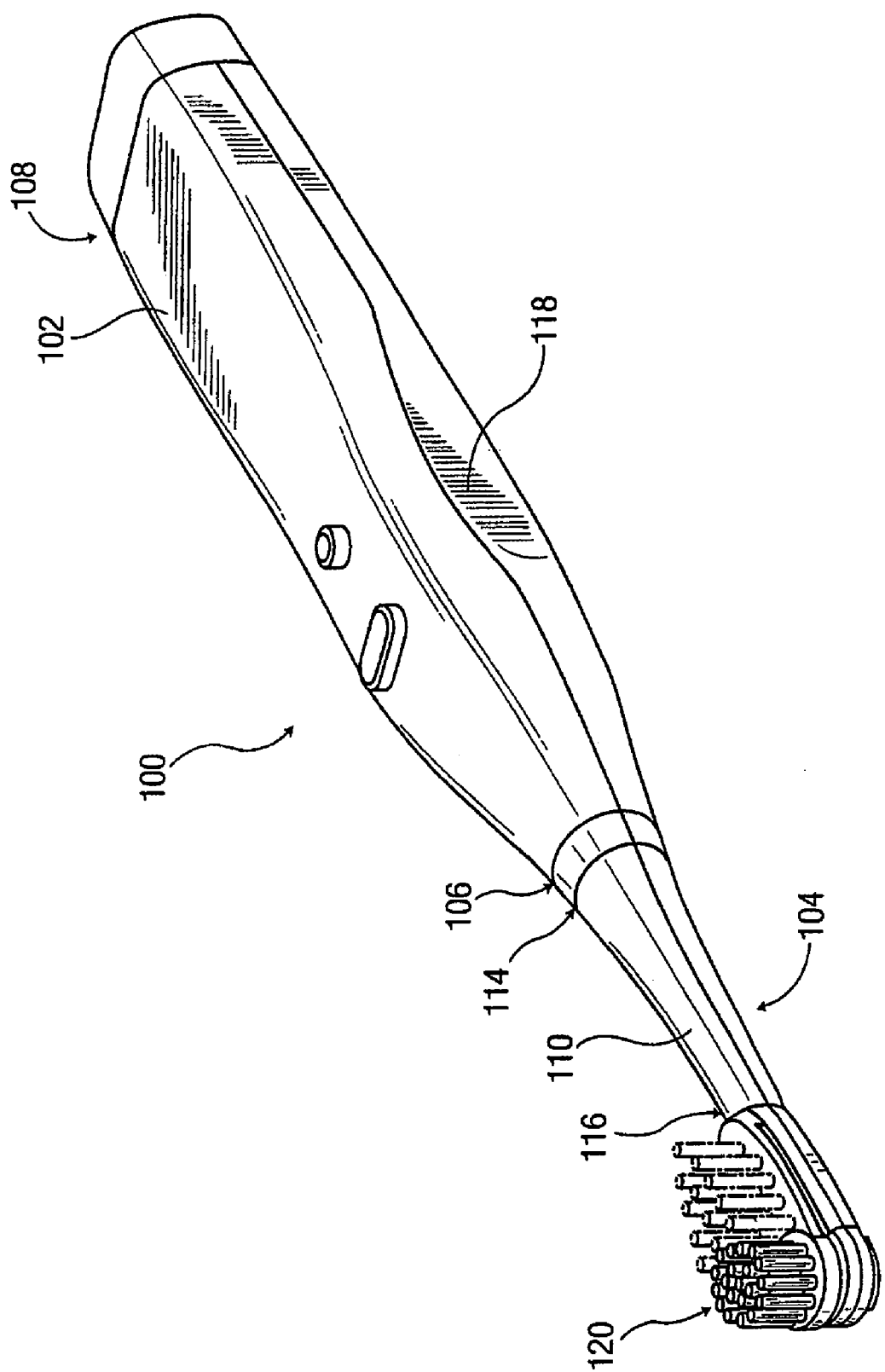
FIG. 2 is a front and side perspective view of a powered toothbrush according to the present invention with a toothbrush head having distinct first and second sections, said second section being shown in general, i.e. dotted lines to indicate that several alternative embodiments are possible for said second section.

The head 120 also includes a first movable bristle carrier 180 which is illustrated as being at the outermost or distal portion of the head 120. The first bristle carrier 180 can have a construction that is either identical to or similar to that of the bristle holder 13 illustrated in FIGS. 1A-1C. The first movable bristle carrier 180 is preferably a disk with a circular cross-section face which it is intended to rotate or oscillate in a rotational manner. However, it will be appreciated that the first movable bristle carrier 180 is not limited to having a disk shape and can have any number of different shapes, such as egg-shaped, an oval or various other regular or irregular shapes, so long as the first moveable bristle carrier 180 can oscillate in a rotational manner. A circular shape is prefer since it requires the least amount of clearance to accommodate the oscillating movement.

A plurality of bristles 152 are coupled to and extend outwardly from the first movable. bristle carrier 180. As used herein, the term "bristles" generally defines tooth care elements and includes any type of structure that is commonly used or is suitable for use in providing oral health benefits (e.g., tooth cleaning, tooth polishing, tooth whitening, etc.) by making intimate contact with surfaces of the teeth and surrounding areas (e.g., gingival tissue). Such bristles include but are not limited to individual bristle strands or tufts of bristles (i.e., a set of bristles) that can be formed to have a number of different shapes and sizes and the bristles can also be in the form of elastomeric members, i.e. elongated elastomeric walls which may be linear or serpentine and/or elastomeric fingers, such as illustrated in FIGS. 19A-19E, or the bristles can include a combination of any of the aforementioned tooth care elements. As illustrated, the arrangement of bristle tufts are only exemplary configurations or bristle patterns and it will be understood that other bristle configurations secured to the head in a conventional way (such as stapled, IMT technology, etc.) can be used and the bristle tufts can be formed of the same or different bristle materials (such as nylon bristles, spiral bristles, rubber bristles, etc.) Moreover, while the bristles can be arranged so that they are generally perpendicular to the surface or face of the toothbrush from which they extend, some or all of the bristles can be angled at various angles with respect to the face of the toothbrush. Using such different configurations, types and angles of bristles helps provide enhanced cleaning and massaging of the teeth and gums, especially in hard to provide areas, such as between the teeth and below the gum line.

Figure 19A:
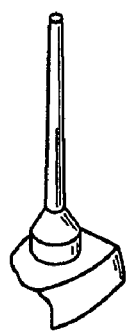
FIG. 19A is a perspective view of an elastomeric tooth care element having a first configuration and adapted for use in the toothbrush head.
Figure 19B:
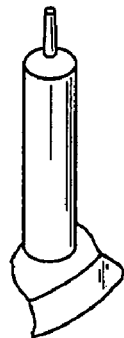
FIG. 19B is a perspective view of an elastomeric tooth care element having a second configuration and adapted for use in the toothbrush head.
Figure 19C:
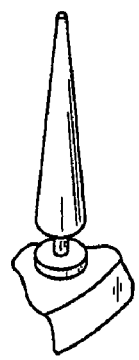
FIG. 19C is a perspective view of an elastomeric tooth care element having a third configuration and adapted for use in the toothbrush head.
Figure 19D:
FIG. 19D is a perspective view of an elastomeric tooth care element having a fourth configuration and adapted for use in the toothbrush head.
Figure 19E:
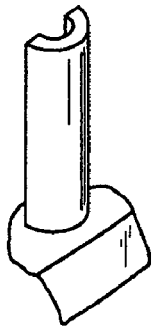

FIGS. 19A-19E illustrate various exemplary elastomeric members that serve as bristles 152. FIG. 19A shows an elastomeric tooth care element in the form of a thin spike; FIG. 19B shows an elastomeric tooth care element in the form of a barrel spike; FIG. 19C shows an elastomeric tooth care element in the form of a squeegee point; FIG. 19D shows an elastomeric tooth care element in the form of an angled point; and FIG. 19E shows an elastomeric tooth care element in the form of a section of an elastomeric wall. The elastomeric wall of FIG. 19E can have a linear, planar shape; a zigzag shape; a serpentine shape, etc. All of the above elastomeric tooth care elements can have smooth textures or can have rough surfaces. In addition, the wall sections of the elastomeric tooth care elements can be vertically straight, taper toward inward toward one end or expand toward one end. The tops of the elastomeric tooth care walls can have a planar surface or can have a protrusion (i.e., hump) or the like formed thereat.

The toothbrush 100 includes a drive mechanism to effectuate movement of certain parts of the toothbrush 100 and more specifically, for causing movement of the first movable bristle carrier 180. Any known geared type of drive structure can be used to oscillate said first movable bristle caner 180, such as disclosed in U.S. Pat. No. 6,000,083 or that disclosed in PCT publication WO 01/19281. One exemplary drive mechanism is disclosed in U.S. Pat. No. 5,625,916 to McDougall, which has been previously incorporated herein by reference and includes a rotating drive shaft 200 that extends at least through the neck 110 (i.e., the inner compartment thereof). The drive shaft 200 preferably ha a construction that is the same as or similar in nature to the shaft 12 illustrated in FIGS. 1A-1C.

The drive mechanism for the powered toothbrush 100 can be any type of drive, e.g., a rotating drive, an oscillating drive, an eccentric drive, an unbalanced-generated drive, a drive having one more gearing mechanisms, and/or the like, that is capable of performing the intended function. The drive mechanism can be realized in the form of an electric motor or other type of motor and the movement generated by the drive can be imparted to one or more sections of the head 120 or to other elements that can be present at the brush section, such as bristle tufts, elastomeric members. The movement can be imparted directly through a driving axle, such as drive shaft 200 or it can be imparted through a driving post attached to the driving axle. When the toothbrush 100 includes an oscillating drive mechanism either identical to or similar to the exemplary drive mechanism illustrated in FIGS. 1A through 1C, the interior compartment of the handle 102 houses a motor operatively connected to the drive shaft 200 and a source to power the motor, such as one or more batteries The toothbrush 100 further includes a second bristle carrier 132 that is operatively mounted on the head 120. The second movable bristle carrier 132 comprises a platform 134 having a first end 136, a second end 138, a first end midpoint 140, a second end midpoint 142, a midpoint, a far side 300, a near side 302, an upper surface 304 and a lower surface. The platform 134 is attached to the head base 160 by supports which may be of such a thin plastic so as to bend readily or of an elastomer, so as to bend readily. In the preferred embodiment, the platform 134 is attached along two sections, at the far side 300 and the near side 302. The platform 134 can be formed of a rigid material or can be formed of an elastomeric material.

The platform 134 may have a weakened section 308 incorporated therein to facilitate movement of the second bristle carrier 132 upon application of a force to the upper surface 304. For example, a longitudinal groove (i.e., a score) 330 can be formed in at least one of the upper surface 304. In the illustrated embodiment, a single groove 330 is formed across the upper surface 304. The groove 330 forms a weakened section 308 longitudinally within the platform 134 (a so called "living hinge" is formed).

FIGS. 4A through 4C illustrate another embodiment of a platform 134 including two grooves 330. Herein, the center section may be deformed about grooves 330 which form hinges when a force A is applied. FIG. 4B illustrates the second bristle carrier 132 in the relaxed condition, prior to any application of force A. FIG. 4C illustrated that when a stress or force, force A, is applied to the face or upper surface 304, the center section may collapse toward the head base 160 and the tooth care elements 152 and the vertical elastomeric elements 340 formed on the upper surface 304 flex inwardly toward one another as a result of such deformation.

Figure 5:
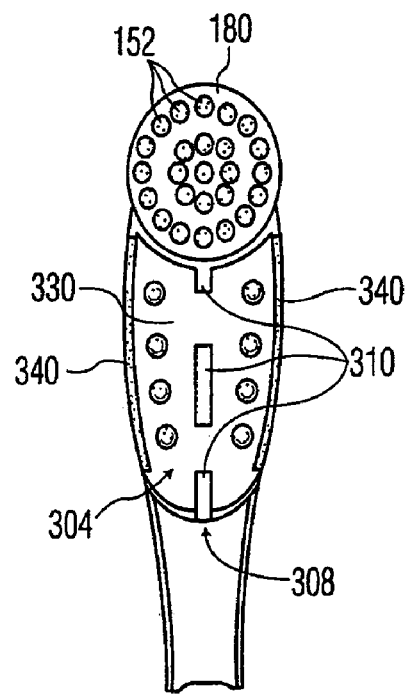
FIG. 5 is a top plan view of an alternate embodiment of the powered toothbrush head of the powered toothbrush embodiment of FIG. 3.

FIG. 5 illustrates the platform 134 with the weakened section 308 in another embodiment wherein openings (slots or gaps) 310 are formed along the weakened section 308 so as to define a number of discrete weakened sections to allow for more flexibility to the hinge.

Figure 6A:
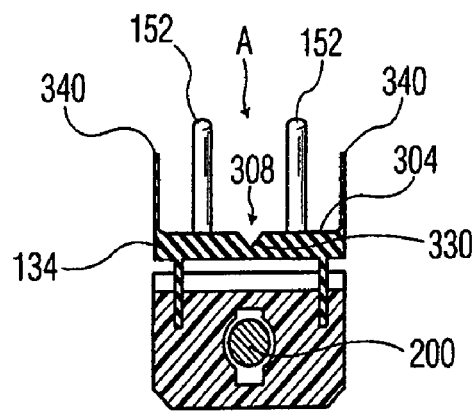
FIGS. 6A-6B are elevated cross-section views of another embodiment of the powered toothbrush head of FIG. 3 in motion.
Figure 6B:
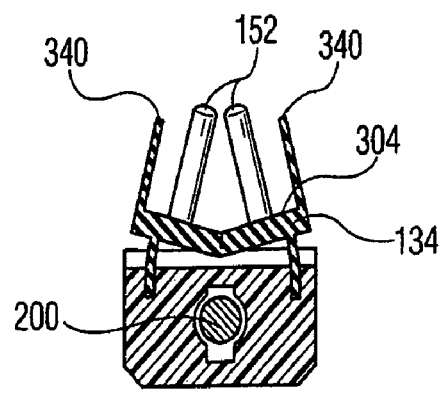

The cross-section of FIG. 6A illustrates another embodiment of the second bristle carrier 132 in a relaxed condition prior to application of a force to the face or upper surface 304. FIG. 6B illustrates the second bristle carrier 132 and platform 134 in a stressed or deformed condition after a force A is applied to the upper surface 304. When a force is applied to the upper surface 304, the upper surface 304 deforms about the hinge created by the one or more grooves 330. This results in the upper surface 304 at least partially collapsing along the hinge section. The bristles 152 formed on the upper surface 304 flex inwardly toward one another as a result of such deformation, as illustrated in FIG. 6B. The elastomeric second bristle carrier 132 can thus be thought of as a hinged block that as shock absorbing characteristics. When the applied force is removed, the second bristle carrier 132 returns to its relaxed condition due to its elastomeric nature.

Figure 7:
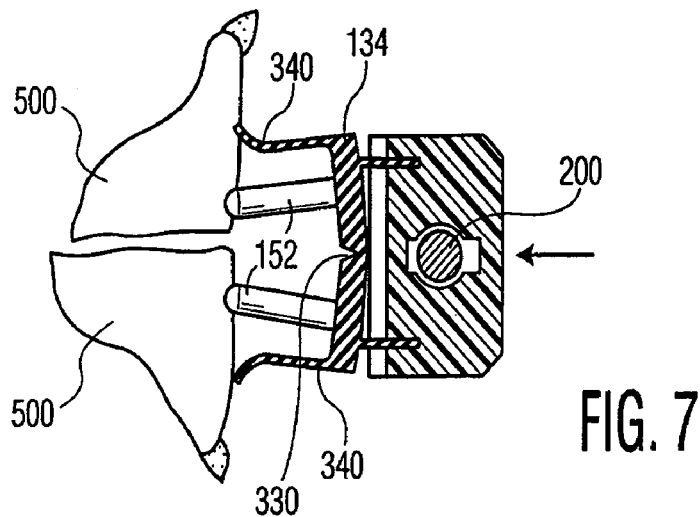
FIG. 7 is a cross-section view of the powered toothbrush head of the powered toothbrush of FIGS. 6a-6b engaging teeth.
Figure 8:
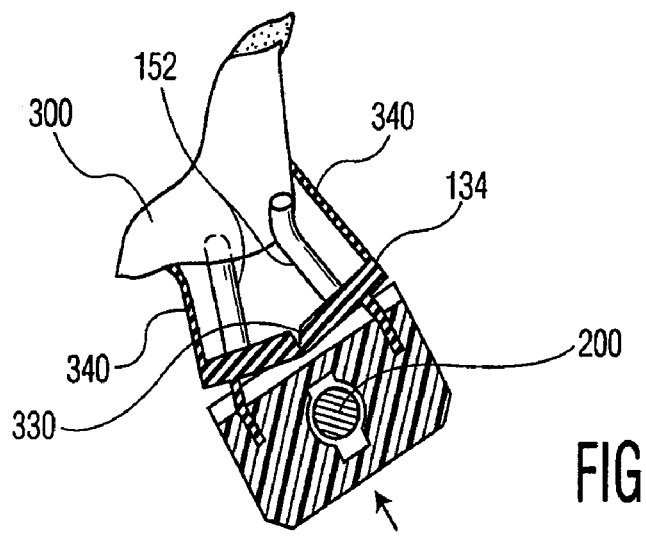
FIG. 8 is a cross-section view of the powered toothbrush head of the powered toothbrush of FIGS. 6a-6b engaging teeth at an oblique angle.

Referring to FIGS. 7 and 8, illustrating the deforming movement when the head 120 is in contact with the teeth 500. FIG. 7 illustrates the second carrier 132 pressed against the side of the teeth 500 and FIG. 8 illustrates the second carrier pressed against the teeth 500 at an oblique angle. Both figures illustrate the deformation of the platform 134 and the bristles and elastomeric elements extending therefrom. The vertical elastomeric element 340 is collapsed upon the surface of the teeth 500 to increase contact. This will enhance cleaning, whitening and massaging.

Preferably, the bristles 152 that extend upwardly from the upper surface 304 are a plurality of elastomeric members (such as those shown in FIGS. 9-11 and 16-18) that are formed integrally with the elastomeric second bristle carrier 132. For example, the bristles 152 can be formed in the same molding operation that forms the elastomeric second bristle carrier 132. Thus, while the elastomeric second bristle carrier 132 is described as a bristle carrier, it will be understood that the carrier 132 need not necessarily have to include traditional nylon bristles.

Figure 3:
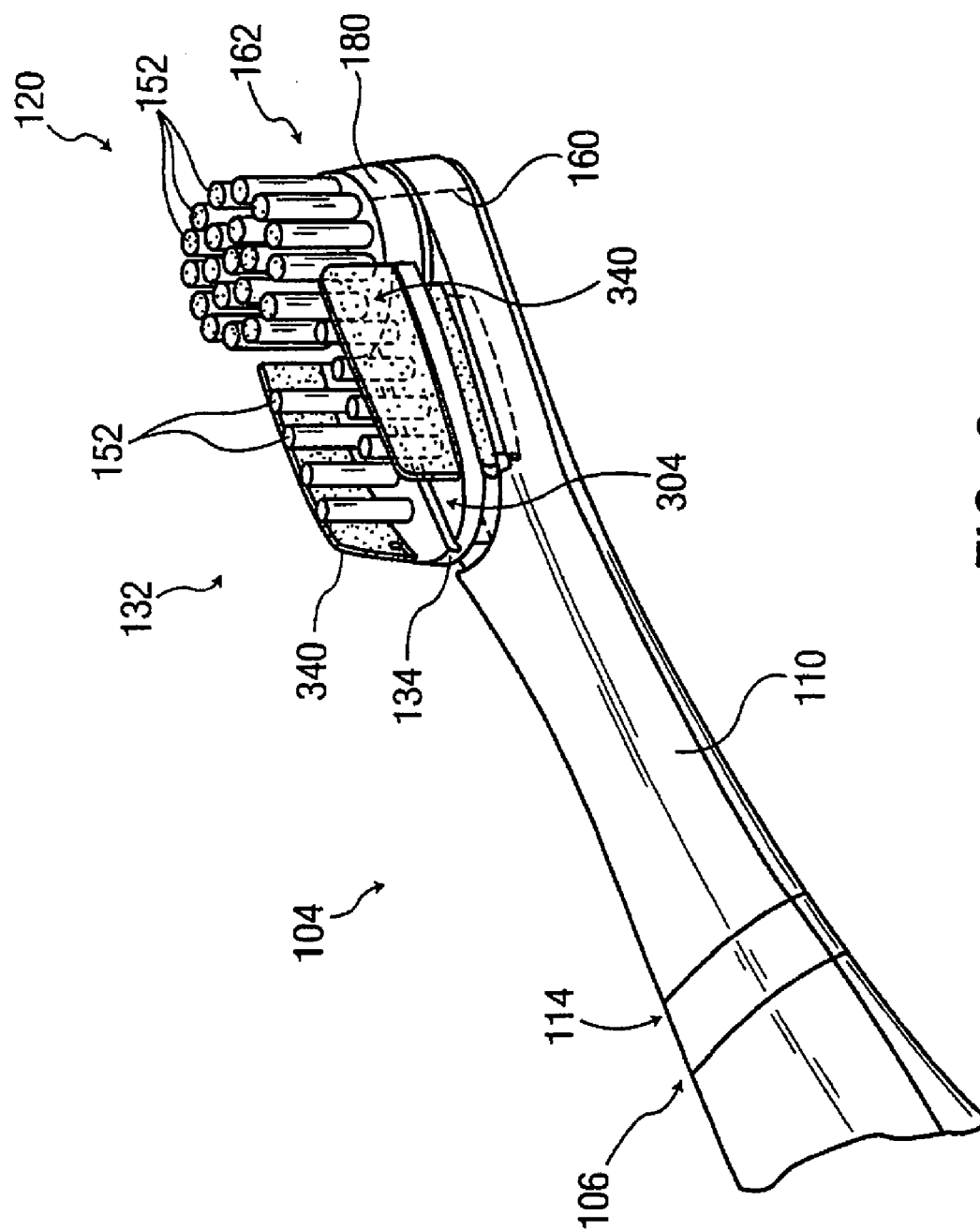
FIG. 3 is a front and side perspective view of an embodiment of the powered toothbrush head of the powered toothbrush of FIG. 2, wherein a particular embodiment of said second section is shown in detail.
Figure 4:
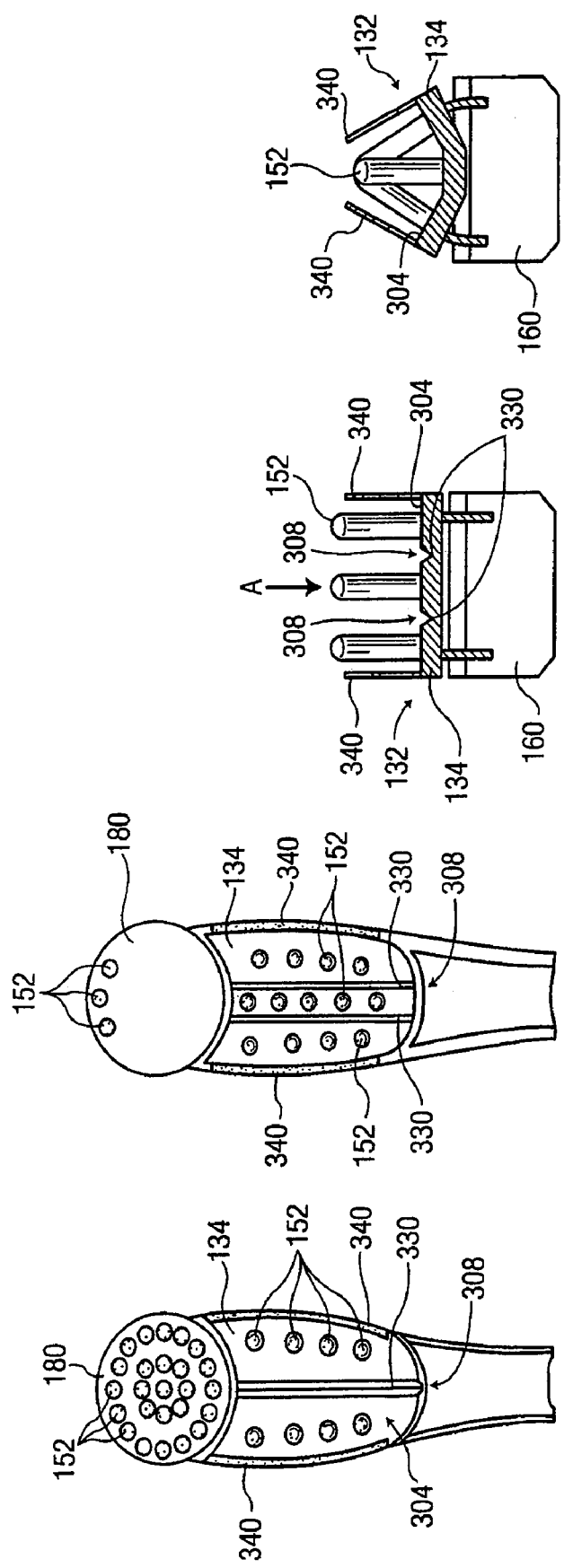
FIG. 4 is a top plan view of the powered toothbrush head of the powered toothbrush embodiment of FIG. 3.
Figure 9:
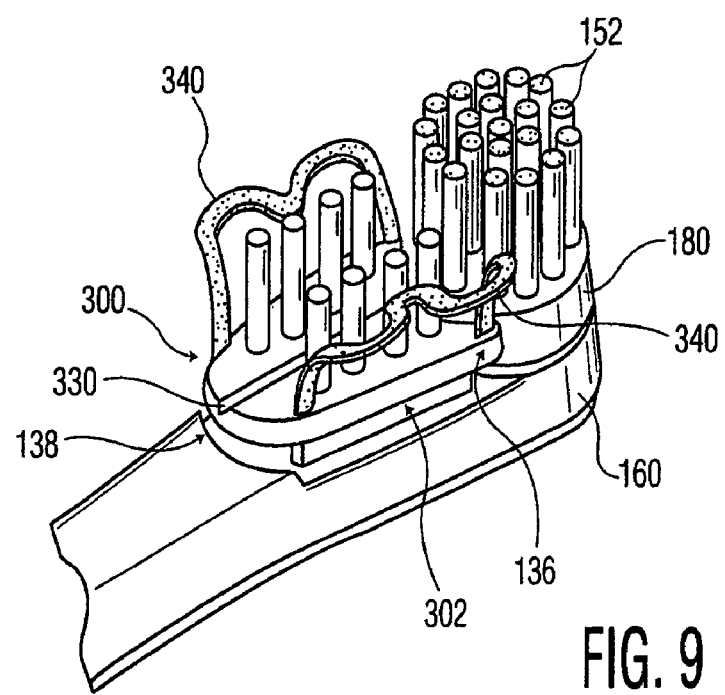
FIG. 9 is a front and side perspective view of the powered toothbrush head of the powered toothbrush of FIG. 2, wherein another embodiment of said second section is shown in detail.
Figure 10:
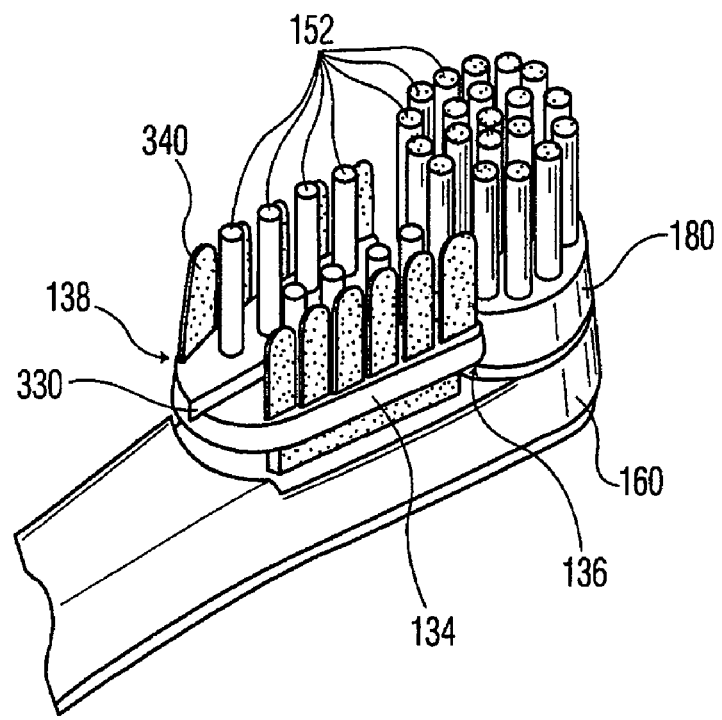
FIG. 10 is a front and side perspective view of the powered toothbrush head of the powered toothbrush of FIG. 2, wherein another embodiment of said second section is shown in detail.
Figure 11:
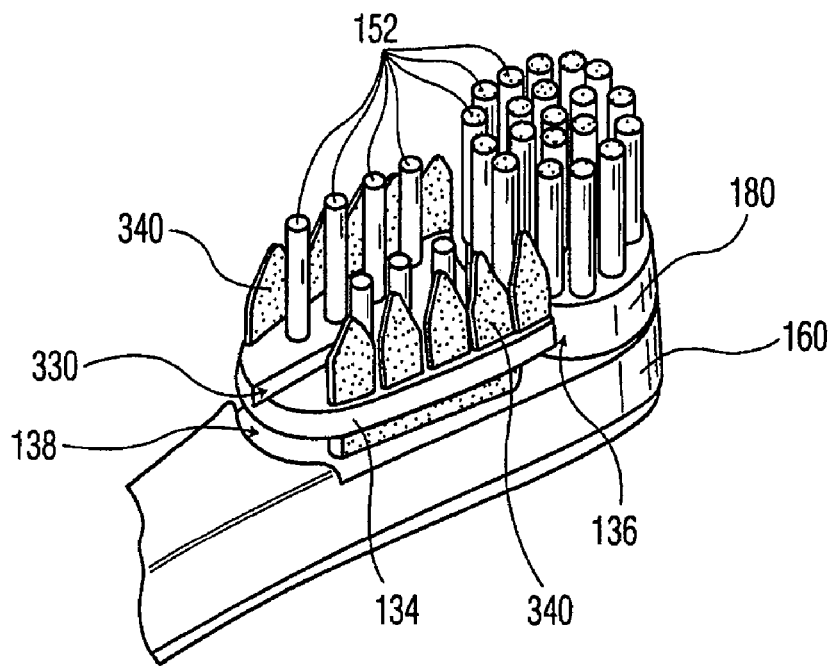
FIG. 11 is a front and side perspective view of the powered toothbrush head of the powered toothbrush of FIG. 2, wherein another embodiment of said second section is shown in detail.
Figure 16:
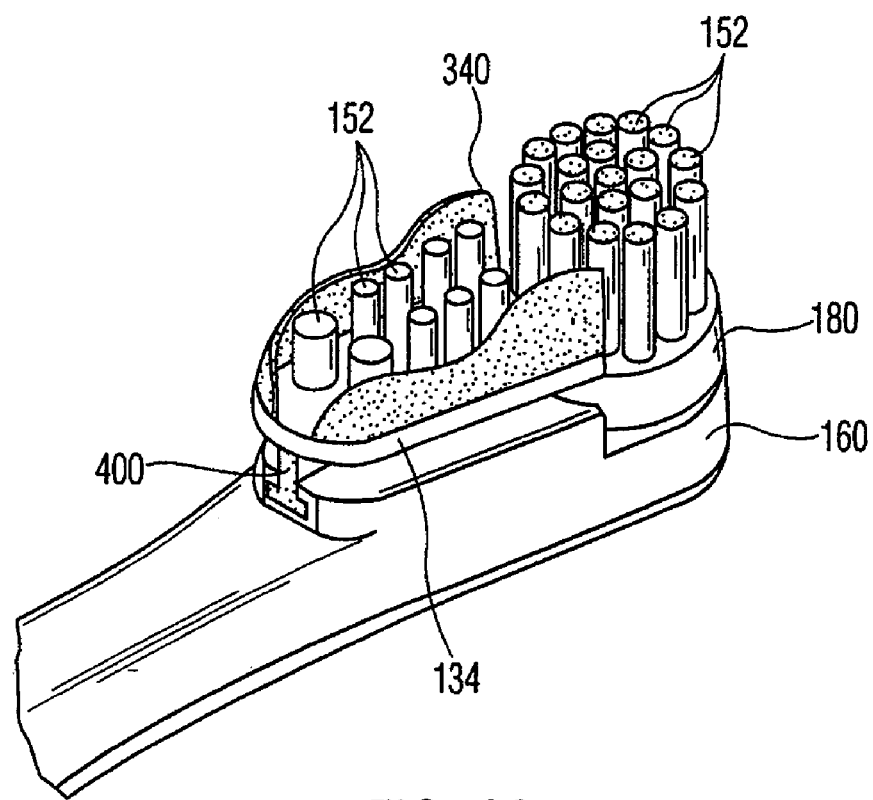
FIG. 16 is a front and side perspective view of the powered toothbrush head of he powered toothbrush of FIG. 2, wherein another embodiment of said second section is shown in detail.
Figure 17:
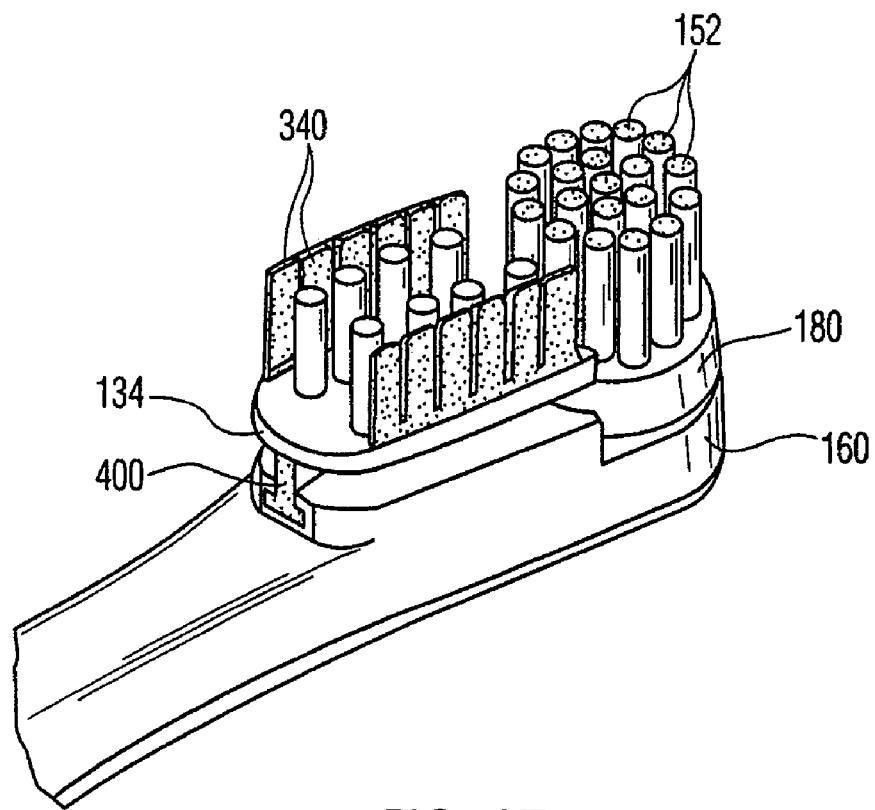
FIG. 17 is a front and side perspective view of the powered toothbrush head of the powered tooth of FIG. 2, wherein another embodiment of said second section is shown in detail.
Figure 18:
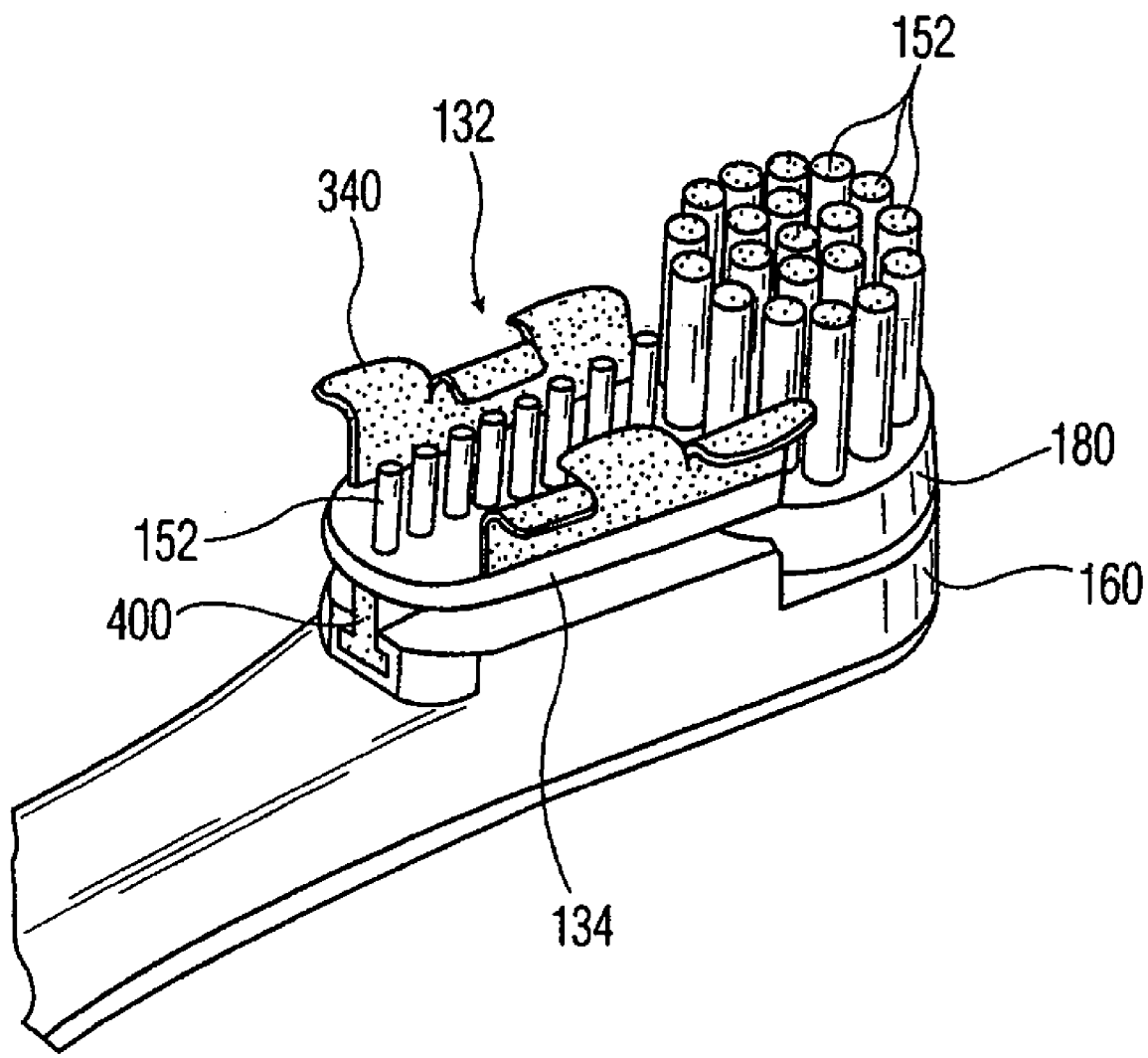
FIG. 18 is a front and side perspective view of the powered toothbrush head of the powered toothbrush of FIG. 2, wherein another embodiment of said second section is shown in detail.

FIGS. 3, 9-11 and 16-18 illustrate numerous elastomeric members/vertical elastomeric elements 340. The vertical elastomeric elements 340 are typically located proximate to the far side 300 and the near side 302 of the platform 134. However, a single vertical elastomeric element or a combination of such vertical elastomeric elements 340 can extend across the width of the second bristle carrier 132. These vertical elastomeric elements 340 may be numerous different shapes and embodiments. FIG. 3 illustrates a straight wall; FIG. 9 illustrates a "butterfly wing", where the element is curvilinear and is only attached proximate to the first end 136 and the second end 138; FIG. 10 illustrates a "paddle" formation, where the element has wide rounded-edge protrusions; FIG. 11 illustrates "dragon teeth"; where the element has a series of short pointed protrusions spaced close together, FIG. 16 illustrates an element that is curvilinear in shape; FIG. 17 illustrates "fingers" narrow, closely spaced protrusions; and FIG. 18 illustrates opposing flaps. It will also be appreciated that any of the forgoing embodiments can be interchanged onto any second carrier regardless of the how or even if that second carrier is hinged or how that second carrier is mounted to the head base 160.

Figure 12:
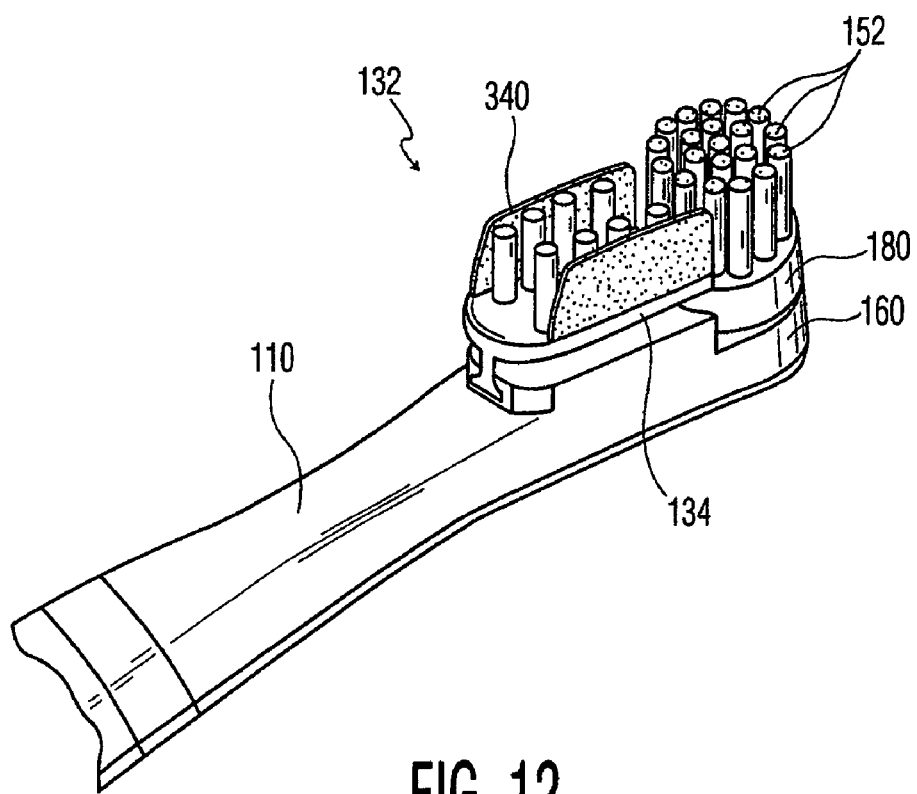
FIG. 12 is a front and side perspective view of another preferred embodiment of the powered toothbrush head of the powered toothbrush of the present invention.
Figure 13:
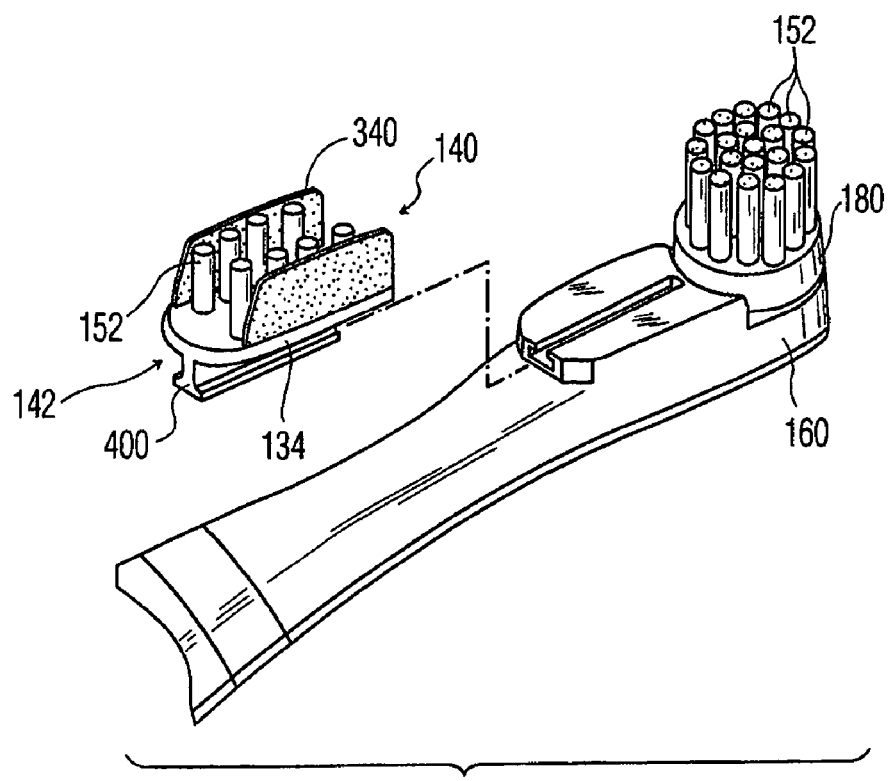
FIG. 13 is a front and side perspective exploded view of the powered toothbrush head of the powered toothbrush of FIG. 12.
Figure 14:
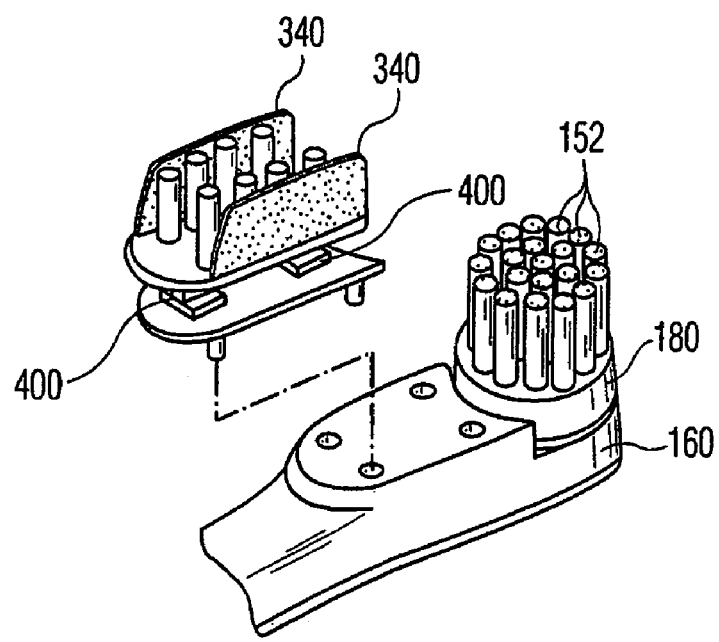
FIG. 14 is a front and side perspective exploded view of another embodiment the powered toothbrush head of the powered toothbrush of FIG. 12.

FIGS. 12 through 18 illustrate views of another exemplary head embodiment of the present invention. The handle 102, neck 110, drive, and head base 160 may be the same as described above. However, referring to FIGS. 12 and 13, the second movable bristle carrier 132 is supported from said head base 160 by an "I-beam" type formation. The platform 134 of the second bristles carrier 132 is supported by an "I-beam" type formation or a web 400 which may be constructed of an elastomeric material possibly with a rigid polymer core to add strength thereto or according to an alternative embodiment, a rigid web 400 can be used in combination with an elastomeric platform 134. The web 400 may extend, in a preferred embodiment from about the first end midpoint 140 to about the second end midpoint 142. The platform 134 can flex and bend about the web 400. FIG. 14 illustrates a plurality of webs 400 spanning the longitudinal length of lower surface of the platform 134.

Figure 15A:
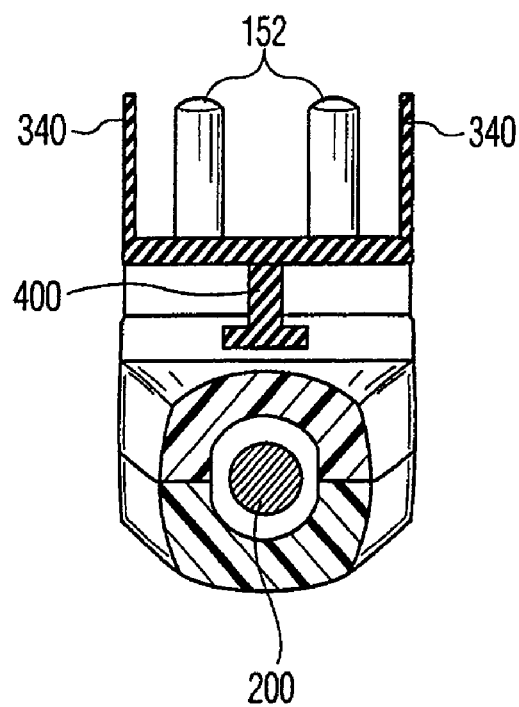
FIGS. 15A-15C are elevated cross-section views of the powered toothbrush head of the embodiment of FIG. 12, in motion.
Figure 15B:
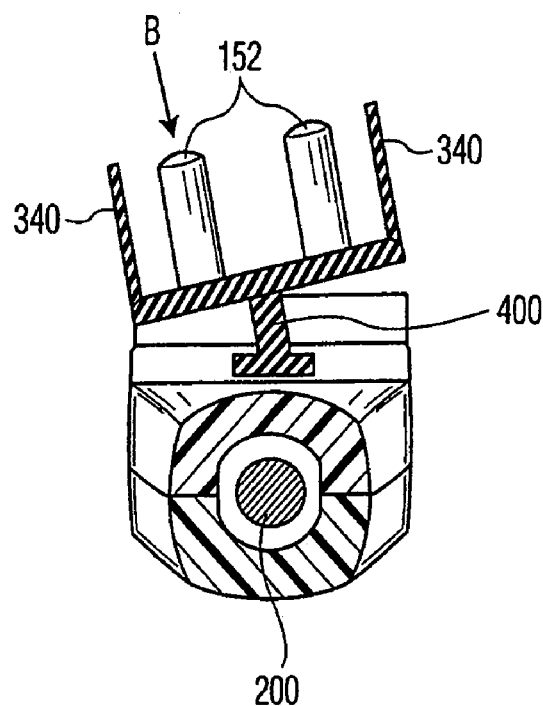
Figure 15C:
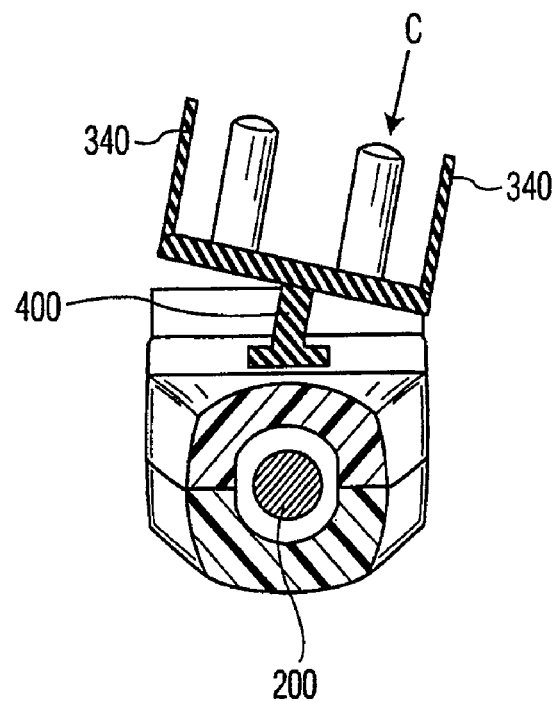

FIGS. 15A-15C illustrate the embodiment of FIGS. 12-14 in motion. FIG. 15B illustrates the platform 134, tilting about the web 400, toward the far side 300 due to force B. FIG. 15C illustrates the platform 134 tilting toward the near side 302 due to a force C and 15A shows the platform 134 at rest.

FIGS. 16-18 illustrate filter embodiments of the vertical elastomeric elements 340 which may be used with the described invention.

It will also be appreciated that in any of the foregoing embodiments, the toothbrush head can have a number of static tooth care elements disposed thereabout in a number of different locations.

The toothbrush 100 according to the various embodiments disclosed herein can be made from any number of materials that are suitable for use in oral care products, such as toothbrushes, etc. For example, many of the components that are included in the toothbrush 100 are formed of plastic materials. Accordingly, the handle 102 and head 120 of the powered toothbrush 100 can be molded from polyolefins such as polypropylenes and polyethylenes, polyamids such as nylons, and polyesters such as polyethylene terephthalate. Other suitable materials include polymethylmethacrylate, styrene acroylonitrate and cellulose esters, for example cellulose propionate.

When the tooth care elements are in the form of tufts of bristles, the bristles of can be made from a flexible material suitable for dental hygiene. Generally, materials suitable for bristles are polyamides such as nylon or polyesters such as polybutylene terephthalate. When the tooth care elements are in the form of elastomeric members, they can be made from any number of suitable elastomeric materials, such as a block copolymer. Preferred block copolymers include styrenes (for example styrene ethylene butadiene styrene, or styrene butadiene styrene), polyolefins (for example polypropylene/ethylene propylene diamine modified systems (i.e. synthetic rubber)), polyamides (for example polyamide (2 or polyamide 6), polyesters (for example polyester ester or polyether ester), polyurethanes (for example polyesterurethane, polyetherurethane or polyesteretherurethane).

Thus, while there have been shown described, and pointed out fundamental novel features of the invention as applied to a preferred embodiment thereof, it will be understood that various omissions, substitutions, and changes in the form and details of the devices illustrated, and in their operation, maybe made by those skilled in the art without departing from the spirit and scope of the invention. For example, it is expressly intended that all combinations of those elements and/or steps which perform substantially the same function, in substantially the same way, to achieve the same results are within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

What is claimed is:

1. A powered toothbrush comprising:
    a handle portion having a neck formed at one end and a drive:
    a head coupled to the neck, the head including (i) a base (ii) at least one bristle portion extending outward, (iii) a pivotal movable part; and (iv) a rotatable movable part including the bristle portion, the rotatable movable part being coupled to the drive for movement and rotatable movable part being movable about a vertical axis extending upwardly from the base;
    the pivotal movable part being resiliently mounted for movement relative to the base about an axis extending generally parallel with respect to the base, the pivotal movable part including (i) a platform having an upper face, and (ii) at least one elastomeric member upstanding on the upper face, and the platform including an elastomeric web extend downwardly and along the axis for said movement, the bristle portion and elastomeric member being adapted to contact teeth and gums.

2. The toothbrush of claim 1 wherein the base gradually narrows to a generally convex end at a rear end of the base in a direction towards the other end of the handle portion.

3. The toothbrush of claim 1 wherein the at least one elastomeric member is curved with respect to the axis.

4. The toothbrush of claim 3 wherein the at least one elastomeric member extends at least partially in a lateral direction along the platform.

5. The toothbrush of claim 1 wherein the at least one elastomeric member is positioned along a perimeter portion of the platform.

6. The toothbrush of claim 1 wherein the at least one elastomeric member comprises elastomeric portions disposed on a perimeter of the platform and a bristle portion is arranged between the elastomeric portions.

7. The toothbrush of claim 6 wherein the elastomeric portions are generally linear.

8. The toothbrush of claim 1 wherein the base includes an opening and the pivotal movable part includes at least one stem received into the opening, the stem including portions that extend laterally beyond the opening to hold the pivotal movable part to the base.

9. The toothbrush of claim 8 wherein the stem and opening are generally aligned along the longitudinal axis of the head.

10. The toothbrush of claim 1 wherein the rotatable moveable part is provided with only a plurality of bristle portions for contacting the teeth and gums.

11. A powered toothbrush comprising:
a handle portion having a neck formed at one end and a drive mechanism;
a head coupled to the neck, the head including (i) a base and (ii) a movable part;
the base having a longitudinal axis and an upper surface to which the movable part is attached; and
the movable part being mounted for freeform pivotal movement about an axis generally parallel to the longitudinal axis of the base and including (i) a platform having a second upper face, (ii) at least one cleaning element extending outward from the second upper face, and (iii) an elastomeric tongue extending in a direction opposite to the cleaning element for receipt in an opening in the base, the elastomeric tongue including portions that extend laterally beyond the opening.

12. The toothbrush of claim 11 wherein the at least one cleaning element is an elastomeric member extending outward from the second upper face.

13. The toothbrush of claim 12 wherein the at least one elastomeric member is formed as an imperforate, elongate wall with an upper edge having a generally uniform height from the second upper face.

14. The toothbrush of claim 13 wherein the at least one elastomeric wall is curved.

15. The toothbrush of claim 12 wherein the at least one elastomeric member is positioned along a perimeter portion of the platform.

16. The toothbrush of claim 12 further including a bristles on the upper face of the base.

17. The toothbrush of claim 11 wherein the head further comprises a second movable part rotatable about an axis extending outward from the upper surface.

* * * * *